(12) United States Patent
Tajima

(10) Patent No.: US 10,653,382 B2
(45) Date of Patent: May 19, 2020

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM CORPORATION, Minato-ku, Tokyo (JP)

(72) Inventor: Takashi Tajima, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 117 days.

(21) Appl. No.: 15/974,703

(22) Filed: May 9, 2018

(65) Prior Publication Data

US 2018/0333126 A1   Nov. 22, 2018

(30) Foreign Application Priority Data

May 18, 2017   (JP) .................................. 2017-099104

(51) Int. Cl.
*A61B 6/00* (2006.01)
*G06T 7/11* (2017.01)
(Continued)

(52) U.S. Cl.
CPC .............. *A61B 6/54* (2013.01); *A61B 6/4241* (2013.01); *A61B 6/461* (2013.01); *A61B 6/463* (2013.01);
(Continued)

(58) Field of Classification Search
CPC ..... A61B 6/4233; A61B 6/461; A61B 6/4291; A61B 6/5258; A61B 8/4416; A61B 8/485; A61B 8/5261; A61B 6/12; A61B 6/505; A61B 6/5235; A61B 6/5217; A61B 6/54; A61B 6/463; A61B 6/465; A61B 6/482; A61B 5/1032; A61B 5/443; A61B 5/0077; G01T 1/2928; G01T 1/208; G06T 2207/10116; G06T 7/0012;
(Continued)

(56) References Cited

U.S. PATENT DOCUMENTS 5,838,758 A * 11/1998 Krug ...................... G01N 23/04
                                                        378/53
6,160,866 A * 12/2000 Mazess ................... A61B 6/032
                                                        378/56
(Continued)

FOREIGN PATENT DOCUMENTS

JP         2011-56257 A      3/2011

*Primary Examiner* — Aklilu K Woldemariam
(74) *Attorney, Agent, or Firm* — Solaris Intellectual Property Group, PLLC

(57) ABSTRACT

A control unit of a console performs a control process of displaying a plurality of images predetermined from at least one of a first radiographic image or a second radiographic image as a simple image, a bone part ES image which is a difference image between the first radiographic image and the second radiographic image and in which a bone tissue is highlighted, a soft part ES image which is a difference image between the first radiographic image and the second radiographic image and in which a soft tissue is highlighted, and a DXA image on a display unit while switching the images and a control process of displaying a derivation result of the bone density and a derivation region on the display unit.

16 Claims, 11 Drawing Sheets

(51) Int. Cl.
*G06T 5/50* (2006.01)
*G06T 7/00* (2017.01)

(52) U.S. Cl.
CPC .............. *A61B 6/482* (2013.01); *A61B 6/505* (2013.01); *A61B 6/5235* (2013.01); *G06T 5/50* (2013.01); *G06T 7/0012* (2013.01); *G06T 7/11* (2017.01); *G06T 2200/24* (2013.01); *G06T 2207/10116* (2013.01); *G06T 2207/20224* (2013.01); *G06T 2207/30008* (2013.01); *G06T 2207/30024* (2013.01)

(58) Field of Classification Search
CPC . G06T 2207/10081; G06T 2207/10016; G06T 2207/30004; G06T 7/32; G06T 7/0014; G06T 2207/30008; G06T 7/60; G06T 2200/24; H04N 5/32; H04N 5/3655; G01N 23/04; G01N 23/20; G06K 9/3233; G06K 9/4647; A61N 2005/1061; A61N 2005/1062; A61N 5/1049; A61F 2/4657; A61F 2/468; G01J 3/50; G06F 19/321; G16H 50/70; A45D 2044/007; A45D 44/005
USPC .............. 378/54, 56, 98; 382/128, 129, 131; 250/394, 370
See application file for complete search history.

(56) References Cited

U.S. PATENT DOCUMENTS

| | | | |
|---|---|---|---|
| 6,246,745 B1 * | 6/2001 | Bi .......................... | A61B 6/463 378/54 |
| 2002/0114425 A1 * | 8/2002 | Lang ..................... | A61B 6/505 378/56 |
| 2002/0136441 A1 * | 9/2002 | Sasada .................. | G06T 5/50 382/132 |
| 2003/0112921 A1 * | 6/2003 | Lang ..................... | A61B 6/505 378/54 |
| 2004/0077088 A1 * | 4/2004 | Charles, Jr. ............ | A61B 6/032 435/455 |
| 2006/0002631 A1 * | 1/2006 | Fu ........................ | G06K 9/3233 382/294 |
| 2011/0243300 A1 * | 10/2011 | Kaneko .................. | A61B 6/06 378/36 |
| 2012/0145912 A1 * | 6/2012 | Iwakiri .................. | A61B 6/06 250/370.08 |
| 2012/0163554 A1 * | 6/2012 | Tada ..................... | A61B 6/4035 378/154 |
| 2014/0198901 A1 * | 7/2014 | Christoff ............... | A61B 6/145 378/98 |
| 2014/0291541 A1 * | 10/2014 | Watanabe .............. | H04N 5/367 250/394 |
| 2016/0113601 A1 * | 4/2016 | Notohara ............. | A61B 6/4035 378/7 |
| 2016/0136458 A1 * | 5/2016 | Taguchi ................ | G06T 11/008 382/132 |
| 2018/0330501 A1 * | 11/2018 | Muraoka ............... | G06T 5/005 |

\* cited by examiner

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATION

This application claims priority under 35 USC 119 from Japanese Patent Application No. 2017-099104 filed May 18, 2017, the disclosure of which is incorporated by reference herein.

BACKGROUND

Technical Field

The present disclosure relates to an image processing apparatus, a radiography system, an image processing method, and an image processing program.

Related Art

In recent years, a technique has been known which derives at least one of the bone density or bone mineral content of a subject on the basis of the detection results of each radiation detector in a radiography apparatus including two radiation detectors that are stacked in a radiation emission direction and are irradiated with radiations having different energy levels (see JP2011-56257A). In the radiography apparatus, one radiation detector that is provided on the incident side of the radiation mainly absorbs a low-energy component of the radiation and generates image data of a radiographic image and the other radiation detector mainly absorbs a high-energy component of the radiation and generates image data of a radiographic image.

SUMMARY

In addition, a method has been known which derives bone density and bone mineral content, using image data (for example, dual-energy X-ray absorptiometry (DXA) image data) generated on the basis of image data of two radiographic images generated by irradiation with (absorption of) radiations having different energy levels. Therefore, it is preferable to improve the accuracy of derivation in the method for deriving the bone density and the bone mineral content and to reduce a burden on the user who performs a derivation operation.

The present disclosure has been made in view of the above-mentioned problems and an object of the present disclosure is to provide an image processing apparatus, a radiography system, an image processing method, and an image processing program that can reduce a burden on a user who performs an operation of deriving at least one of bone density or bone mineral content.

In order to achieve the object, the present disclosure provides an image processing apparatus comprising: an acquisition unit that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; a derivation unit that derives at least one of bone mineral content or bone density from a derivation region of a difference image for derivation which is a difference image between the first radiographic image and the second radiographic image and is used to derive at least one of the bone density or the bone mineral content; and a control unit that performs a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result of the derivation unit or the derivation region on the display unit.

In order to achieve the object, the present disclosure provides an image processing apparatus comprising: an acquisition unit that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; a derivation unit that derives at least one of bone mineral content or bone density from a derivation region of a difference image for derivation which is a difference image between the first radiographic image and the second radiographic image and is used to derive at least one of the bone density or the bone mineral content; and a control unit that performs a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result of the derivation unit or the derivation region on the display unit.

In order to achieve the object, the present disclosure provides an image processing apparatus comprising: an acquisition unit that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; a derivation unit that derives at least one of bone mineral content or bone density from a derivation region of a difference image for derivation which is a difference image between the first radiographic image and the second radiographic image and is used to derive at least one of the bone density or the bone mineral content; and a control unit that performs a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side on a display unit and a control process of displaying at least one of a derivation result of the derivation unit or the derivation region on the display unit.

In order to achieve the object, the present disclosure provides an image processing apparatus comprising: an acquisition unit that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; a derivation unit that derives at least one of bone mineral content or bone density from a derivation region of a difference image for derivation which is a difference image between the first radiographic image and the second radiographic image and is used to derive at least one of the bone density or the bone mineral content; and a control unit that performs a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side on a display unit and a control process of displaying at least one of a derivation result of the derivation unit or the derivation region on the display unit.

The image processing apparatus according to the present disclosure may further comprise a detection unit that detects a region indicated by a user in the image displayed on the display unit. The control unit may perform a control process of displaying any one of the at least one of the first radiographic image or the second radiographic image, the bone part difference image in which the bone tissue is highlighted, the soft part difference image, and the difference image for derivation which has been predetermined according to a tissue corresponding to the region detected by the detection unit on the display unit.

In the image processing apparatus according to the present disclosure, the control unit may perform a control process of displaying the bone part difference image on the display unit in a case in which the region detected by the detection unit corresponds to the bone tissue and displaying the soft part difference image on the display unit in a case in which the region detected by the detection unit corresponds to the soft tissue.

In the image processing apparatus according to the present disclosure, the control unit may perform a control process of displaying the soft part difference image on the display unit in a case in which the region detected by the detection unit corresponds to the bone tissue and displaying the bone part difference image on the display unit in a case in which the region detected by the detection unit corresponds to the soft tissue.

In the image processing apparatus according to the present disclosure, the control unit may perform a control process of further displaying a profile indicating a relationship between a pixel position and a pixel value in the derivation region on the display unit.

In the image processing apparatus according to the present disclosure, the control unit may perform a control process of displaying at least the derivation region so as to be superimposed on the image displayed on the display unit.

The image processing apparatus according to the present disclosure may further comprise a receiving unit that receives a change in the derivation region. In a case in which the receiving unit receives the change, the derivation unit may derive at least one of the bone mineral content or the bone density from the changed derivation region.

In the image processing apparatus according to the present disclosure, each of the first and second radiation detectors may comprise a light emitting layer that is irradiated with the radiation and emits light. The plurality of pixels of each of the first and second radiation detectors may receive the light, generate the charge, and accumulate the charge. The light emitting layer of one of the first and second radiation detectors which is provided on an incident side of the radiation may include CsI and the light emitting layer of the other radiation detector may include GOS.

In order to achieve the object, the present disclosure provides a radiography system comprising: the image processing apparatus according to the present disclosure; and a radiography apparatus that outputs a first radiographic image and a second radiographic image to the image processing apparatus.

In order to achieve the object, the present disclosure provides an image processing method comprising: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result or the derivation region on the display unit.

In order to achieve the object, the present disclosure provides an image processing method comprising: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result or the derivation region on the display unit.

In order to achieve the object, the present disclosure provides an image processing method comprising: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side on a display unit and a control process of displaying at least one of a derivation result or the derivation region on the display unit.

In order to achieve the object, the present disclosure provides an image processing method comprising: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side on a display unit and a control process of displaying at least one of a derivation result or the derivation region on the display unit.

In order to achieve the object, the present disclosure provides a non-transitory recording medium recording an image processing program that causes a computer to perform: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result or the derivation region on the display unit.

In order to achieve the object, the present disclosure provides a non-transitory recording medium recording an image processing program that causes a computer to perform: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result or the derivation region on the display unit.

In order to achieve the object, the present disclosure provides a non-transitory recording medium recording an image processing program that causes a computer to perform: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side on a display unit and a control process of displaying at least one of a derivation result or the derivation region on the display unit.

In order to achieve the object, the present disclosure provides a non-transitory recording medium recording an image processing program that causes a computer to perform: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side on a display unit and a control process of displaying at least one of a derivation result or the derivation region on the display unit.

According to the present disclosure, it is possible to reduce a burden on a user who performs an operation of deriving at least one of bone density or bone mineral content.

BRIEF DESCRIPTION OF THE DRAWINGS

Exemplary Embodiments of the present invention will be described in detail with reference to the following figures, wherein.

DETAILED DESCRIPTION

Hereinafter, embodiments of the present disclosure will be described in detail with reference to the drawings.

First Embodiment

Figure 1:
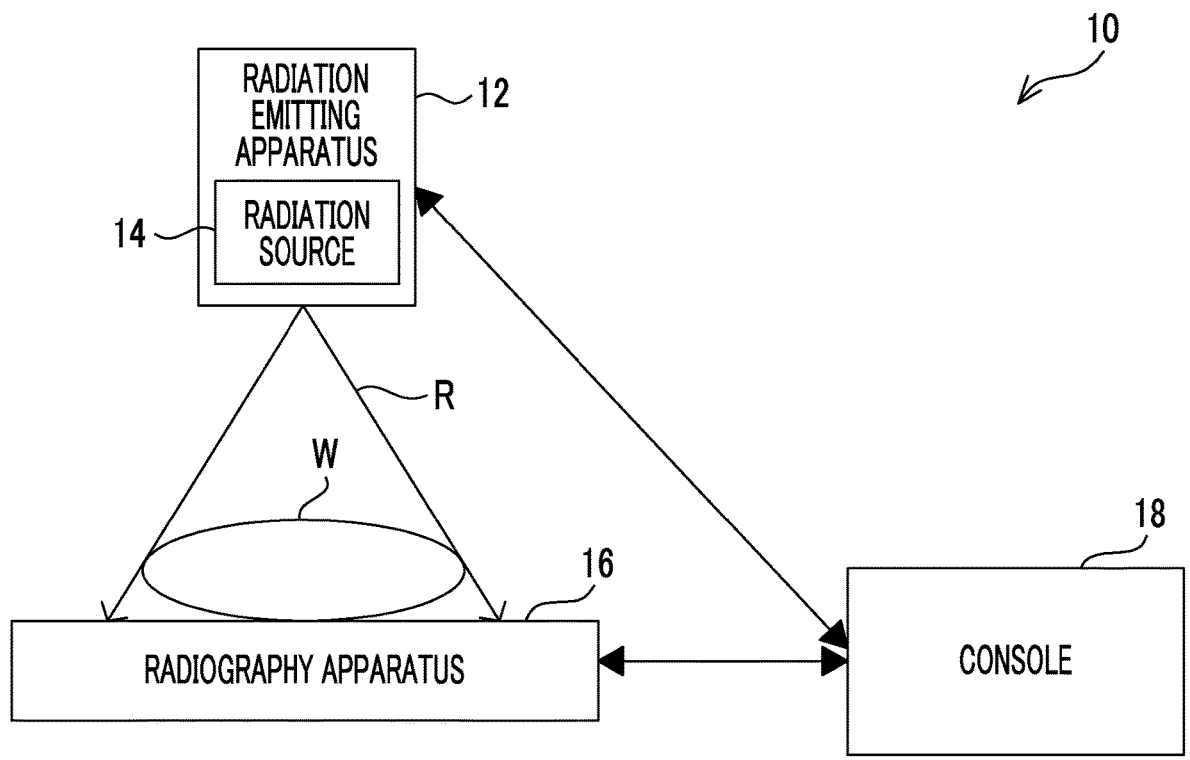
FIG. 1 is a block diagram illustrating an example of the configuration of a radiography system according to each embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. In this embodiment, the console 18 is an example of an image processing apparatus according to the present disclosure.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

When receiving the command to emit the radiation R, the radiation emitting apparatus 12 emits the radiation R from the radiation source 14 according to set exposure conditions, such as a tube voltage, a tube current, and an irradiation period. Hereinafter, the dose of the radiation R is simply referred to as "the amount of radiation".

Figure 2:
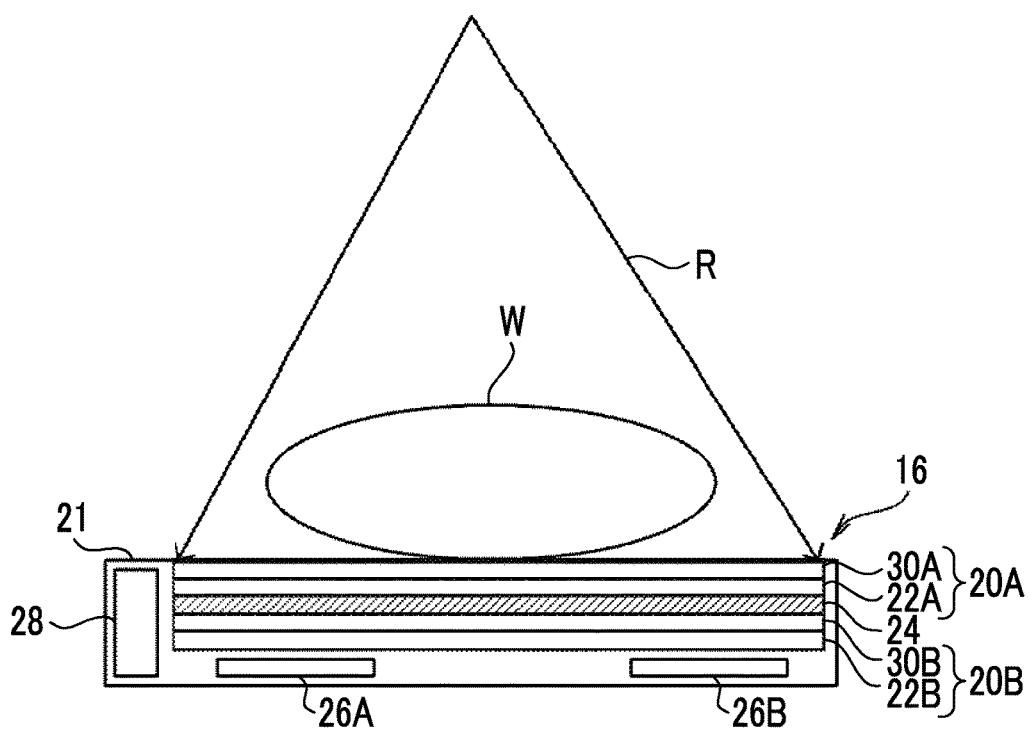
FIG. 2 is a side cross-sectional view illustrating an example of the configuration of a radiography apparatus according to a first embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes a first radiation detector 20A and a second radiation detector 20B that detect the radiation R transmitted through the subject W. In addition, the housing 21 includes a radiation limitation member 24, a control substrate 26A, a control substrate 26B, and a case 28. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

The first radiation detector 20A is provided on the incident side of the radiation R in the radiography apparatus 16 and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) as a main component and the scintillator 22B includes gadolinium oxysulfide (GOS) as a main component. GOS has a higher sensitivity to the high-energy radiation R than CsI. In addition, a combination of the composition of the scintillator 22A and the composition of the scintillator 22B is not limited to the above-mentioned example and may be a combination of other compositions or a combination of the same compositions.

For example, the scintillators 22A and 22B have emission characteristics that vary depending on a thickness. As the thickness increases, the amount of light emitted increases and sensitivity increases. However, image quality deteriorates due to, for example, light scattering.

For example, in a case in which the scintillators 22A and 22B are formed by being filled with particles which are irradiated with the radiation R and emit light, such as GOS particles, as the diameter of the particle increases, the amount of light emitted increases and sensitivity increases. However, the amount of light scattering increases and the increase in the amount of light scattering affects adjacent pixels 32 (see FIG. 3), which results in the deterioration of image quality.

In addition, the scintillators 22A and 22B may have a stacked structure of a small-particle layer and a large-particle layer. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, image blurring is small in the scintillators 22A and 22B in which a region close to the irradiation side of the radiation R is filled with small particles and a region close to the side of the TFT substrate 30 that is the emission side of the radiation R is filled with large particles. However, oblique components of light that is radially emitted by the small particles are less likely to reach the TFT substrates 30A and 30B and sensitivity is reduced. In addition, in a case in which the ratio of the region filled with small particles to the region filled with large particles is changed such that the number of layers formed by the region filled with large particles is larger than the number of layers formed by the region filled with small particles, sensitivity increases. However, in this case, light scattering affects adjacent pixels 32, which results in the deterioration of image quality.

As the filling rate of the particles increases, the sensitivity of the scintillators 22A and 22B increases. However, the amount of light scattering increases and image quality deteriorates. Here, the filling rate is a value obtained by dividing the total volume of the particles of the scintillator 22A or 22B by the volume of the scintillator 22A or 22B and multiplying the divided value by 100 (the total volume of the particles of the scintillator 22A or 22B/the volume of the scintillator 22A or 22B×100). In addition, powder is treated in the scintillators 22A and 22B. Therefore, in a case in which the filling rate is greater than 80%, it is difficult to manufacture the scintillators 22A and 22B. For this reason, it is preferable that the filling rate is in the range of 50 vol % to 80 vol %.

In addition, the emission characteristics of the scintillators 22A and 22B vary depending on the doping amount of activator. As the doping amount of activator increases, the amount of light emitted tends to increase. However, the amount of light scattering increases and image quality deteriorates.

The emission characteristics of the scintillators 22A and 22B with respect to the radiation R vary depending on the material used for the scintillators 22A and 22B. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the scintillator 22A is made of GOS and the scintillator 22B is made of CsI (Tl) in order to put emphasis on sensitivity in the scintillator 22A and to put emphasis on image quality in the scintillator 22B.

In addition, the emission characteristics of the scintillators 22A and 22B with respect to the radiation R vary depending on whether the scintillators 22A and 22B have a plate-shaped layer structure or a columnar separated layer structure.

For example, the scintillator 22A is configured to have the plate-shape layer structure and the scintillator 22B is configured to have the columnar separated layer structure in order to put emphasis on sensitivity in the scintillator 22A and to put emphasis on image quality in the scintillator 22B.

In a case in which reflecting layers that transmit the radiation R and reflect visible light are formed on the sides of the TFT substrates 30A and 30B which are opposite to the scintillators 22A and 22B, light generated by the scintillators 22A and 22B is more effectively guided to the TFT substrates 30A and 30B and sensitivity is improved. A method for forming the reflecting layer is not particularly limited. For example, any of a sputtering method, a vapor deposition method, and a coating method may be used to form the reflecting layer. It is preferable that the reflecting layer is made of a material with high reflectance in an emission wavelength range of the scintillators 22A and 22B used. For example, the reflecting layer is made of Au, Ag, Cu, Al, Ni, and Ti. For example, in a case in which the scintillators 22A and 22B are made of GOS:Tb, the reflecting layer is preferably made of Ag, Al, and Cu that have high reflectance in a wavelength of 400 nm to 600 nm. In a case in which the thickness of the reflecting layer is less than 0.01 μm, reflectance is not obtained. Even in a case in which the thickness is greater than 3 μm, the effect of further improving the reflectance is not obtained. For this reason, it is preferable that the thickness of the reflecting layer is in the range of 0.01 μm to 3 μm.

Therefore, the characteristics of the scintillators 22A and 22B may vary depending on the diameter of particles, the multi-layered structure of particles, the filling rate of particles, the doping amount of activator, a material, a change in layer structure, and the shape of the reflecting layer.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that a variation in the thickness of the radiation limitation member 24 in the incident direction of the radiation R is equal to or less than 1% in order to uniformize the limitation (transmittance) of the radiation. In a case in which the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the configuration of a main portion of an electric system of the radiography apparatus 16 according to this embodiment will be described with reference to FIG. 3.

Figure 3:
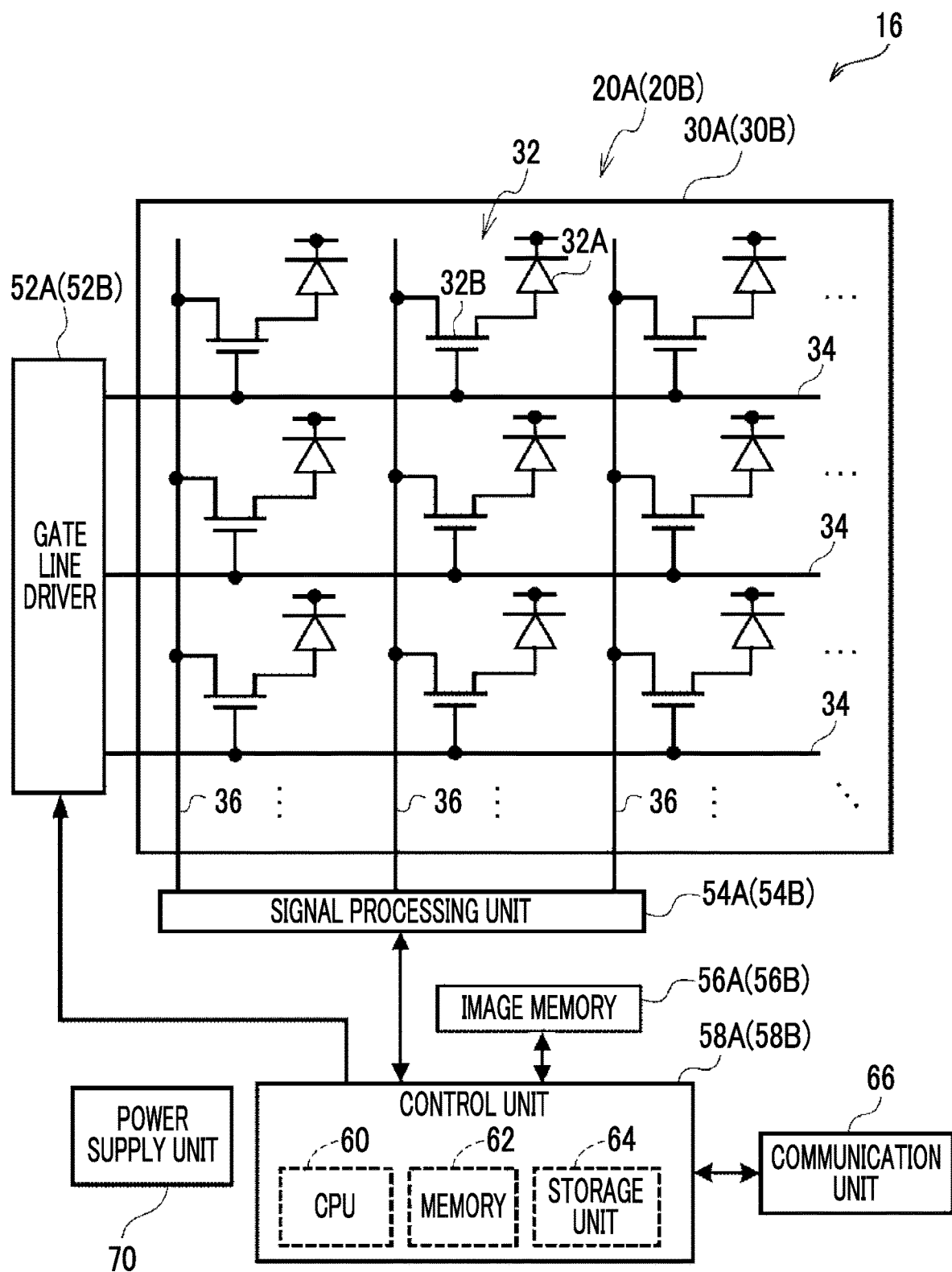
FIG. 3 is a block diagram illustrating an example of the configuration of a main portion of an electric system of a radiography apparatus according to each embodiment.

As illustrated in FIG. 3, a plurality of pixels 32 are two-dimensionally provided in one direction (a row direction in FIG. 3) and a cross direction (a column direction in FIG. 3) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B reads the charge accumulated in the sensor unit 32A, converts the charge into an electric signal, and outputs the electric signal in response to a control signal. The sensor unit 32A is an example of a conversion element that generates a larger amount of charge as the amount of radiation becomes larger.

A plurality of gate lines 34 which extend in the one direction and are used to turn each thin film transistor 32B on and off are provided on the TFT substrate 30A. In addition, a plurality of data lines 36 which extend in the cross direction and are used to read out the charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The thin film transistors 32B corresponding to each gate line 34 on the TFT substrate 30A are sequentially turned on (in units of rows illustrated in FIG. 3 in this embodiment) by control signals which are supplied from the gate line driver 52A through the gate lines 34. Then, the charge which has been read by the thin film transistor 32B in an on state is transmitted as an electric signal through the data line 36 and is input to the signal processing unit 54A. In this way, charge is sequentially read from each gate line 34 (in units of rows illustrated in FIG. 3 in this embodiment) and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data". Furthermore, the "first radiographic image" and the "second radiographic image" are generically referred to as "simple images".

Figure 4:
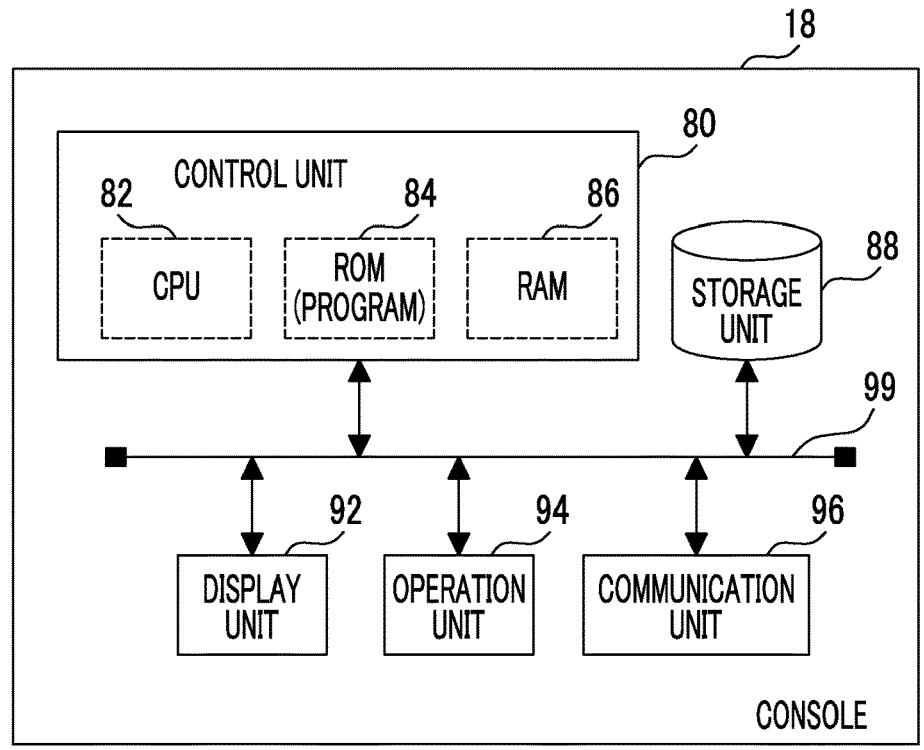
FIG. 4 is a block diagram illustrating an example of the configuration of a main portion of an electric system of a console according to each embodiment.

Next, the configuration of the console 18 according to this embodiment will be described with reference to FIG. 4. As illustrated in FIG. 4, the console 18 includes a control unit 80. The control unit 80 includes a CPU 82 that controls the overall operation of the console 18, a ROM 84 in which, for example, various programs or various parameters are stored in advance, and a RAM 86 that is used as, for example, a work area when the CPU 82 executes various programs.

In addition, the console 18 includes a non-volatile storage unit 88 such as a hard disk drive (HDD). The storage unit 88 stores and holds image data indicating the radiographic image captured by the first radiation detector 20A, image data indicating the radiographic image captured by the second radiation detector 20B, and various other data items.

The console 18 further includes a display unit 92, an operation unit 94, and a communication unit 96. The display unit 92 displays, for example, information related to imaging and a captured radiographic image. The operation unit 94 is used by a user to input a command to capture a radiographic image and a command to perform image processing for the captured radiographic image. For example, the operation unit 94 may have the form of a keyboard or the form of a touch panel integrated with the display unit 92. The communication unit 96 transmits and receives various kinds of information to and from the radiography apparatus 16 and the radiation emitting apparatus 12, using at least one of wireless communication or wired communication. In addition, the communication unit 96 transmits and receives various kinds of information to and from the external systems, such as a picture archiving and communication system (PACS) and a radiology information system (RIS), using at least one of wireless communication or wired communication.

The control unit 80, the storage unit 88, the display unit 92, the operation unit 94, and the communication unit 96 are connected to each other through a bus 99.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
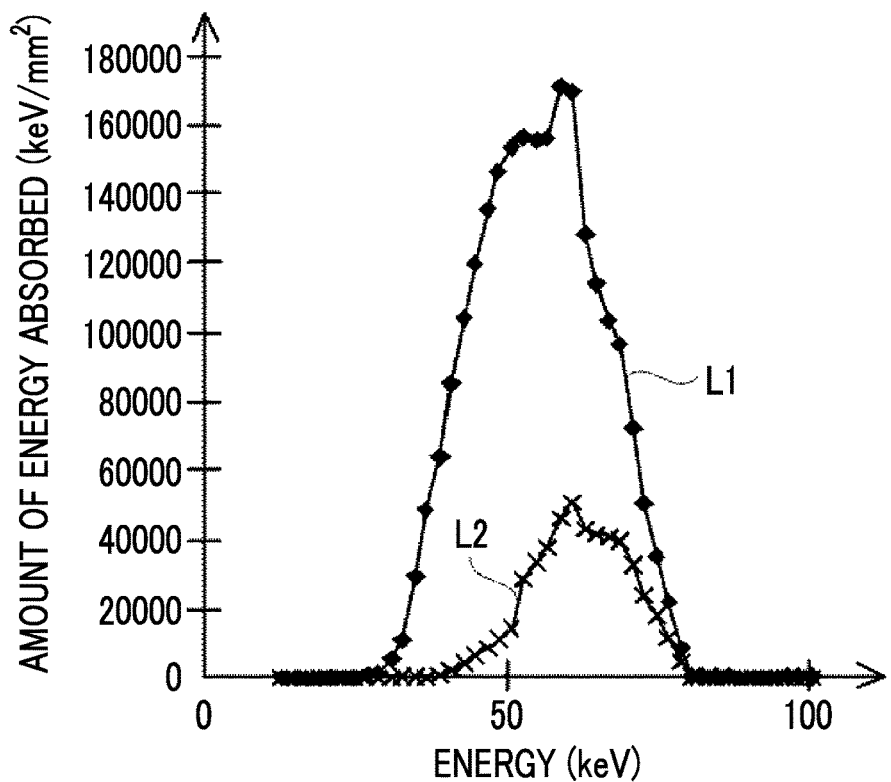
FIG. 5 is a graph illustrating the amount of radiation that reaches each of a first radiation detector and a second radiation detector.

Low-energy components of the radiation R are absorbed first. The radiation R absorbed by each of the first radiation detector 20A and the second radiation detector 20B will be described with reference to FIG. 5. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed per unit area. In addition, in FIG. 5, a solid line L2 indicates the relationship between the energy of the radiation R absorbed by the second radiation detector 20B and the amount of radiation R absorbed per unit area. Since the low-energy components of the radiation R are absorbed first, for example, as illustrated in FIG. 5, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to this embodiment, the radiation detectors 20 are irradiated with the radiations R having different energy levels and radiographic images are generated by the radiation detectors 20.

The console 18 according to this embodiment acquires radiographic image data generated by the radiation detectors 20 irradiated with the radiations R having different energy levels (radiation R with a first energy level and radiation R with a second energy level). In addition, the console 18 derives the ratio of the values of the corresponding pixels of first radiographic image data and second radiographic image data and generates image data for deriving the bone density of the subject W. Hereinafter, the image data for deriving the bone density of the subject W is referred to as "dual-energy X-ray absorptiometry (DXA) image data" and an image indicated by the DXA image data is referred to as a "DXA image". Specifically, the console 18 performs log conversion for each pixel value of each of the first radiographic image data and the second radiographic image data. Then, the console 18 subtracts image data obtained by performing log conversion for the second radiographic image data from image data obtained by performing log conversion for the first radiographic image data for each corresponding pixel to generate DXA image data. As such, the DXA image according to this embodiment is a difference image between a first radiographic image and a second radiographic image, is an image used to derive bone density, and is an example of a difference image for derivation according to the present disclosure.

Figure 6:
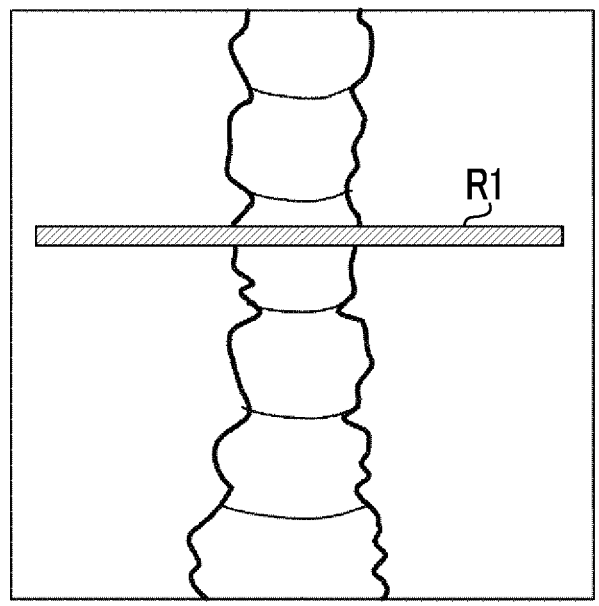
FIG. 6 is a front view illustrating an example of a region from which a DXA profile used to derive bone density is to be derived.

In addition, for example, as illustrated in FIG. 6, the console 18 according to this embodiment derives bone density from each pixel value (that is, the ratio of the values of the corresponding pixels of the first radiographic image and the second radiographic image) of the bone of the subject W in the cross-sectional direction (the horizontal direction in the example illustrated in FIG. 6) in the DXA image.

Figure 7:
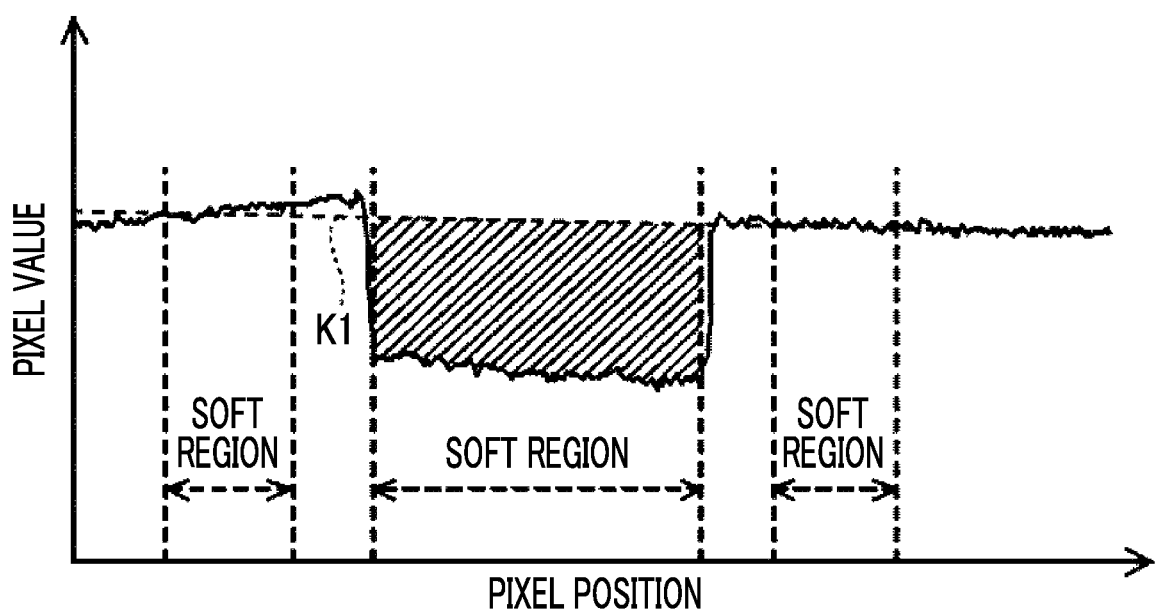
FIG. 7 is a graph illustrating a bone density derivation process.

FIG. 7 illustrates the value of each pixel in a derivation region R1 of the DXA image illustrated in FIG. 6. In FIG. 7, the horizontal axis indicates a pixel position in the horizontal direction of FIG. 6. In addition, in FIG. 7, the vertical axis indicates an average value of the values of a plurality of pixels in the vertical direction of FIG. 6 at each pixel position in the horizontal direction of FIG. 6. Hereinafter, a data group of the pixel values at each pixel position along the horizontal direction of FIG. 6 which is illustrated in FIG. 7 is referred to as a "DXA profile". The DXA profile according to this embodiment is an example of a profile according to the present disclosure which indicates the relationship between the position of the pixel and the pixel value in the derivation region.

As illustrated in FIG. 7, for the pixel values in the DXA profile, a pixel value at a pixel position corresponding to the bone tissue of the subject W is less than a pixel value at a pixel position corresponding to the soft tissue. The console 18 according to this embodiment derives the average value of the pixel values in soft tissue regions (hereinafter, referred to as "soft regions") on both sides of a bone tissue region (hereinafter, referred to as a "bone region") and derives a straight line (hereinafter, referred to as a "reference line") K1 that connects the average values derived at the pixel positions in a central portion of each soft region. In addition, the console 18 adds the differences between the reference line K1 and the pixel values at each pixel position in the bone region to derive the area of the bone region (the area of a hatched portion illustrated in FIG. 7). The area is a value corresponding to the bone mass of the subject W. For example, the bone region is separated from the soft region by a predetermined number of pixels in FIG. 7 in order to prevent the influence of noise caused by light scattered by the bone.

In addition, the console 18 divides the derived area by the number of pixels corresponding to the width of the bone region to derive the difference between the pixel values of the bone region and the soft region per unit number of pixels. The difference is a value corresponding to the bone density of the subject W. Then, the console 18 multiplies the derived difference between the pixel values of the bone region and the soft region per unit number of pixels by a predetermined unit conversion coefficient to derive the bone density of the subject W. In this embodiment, the pixel position of the derivation region R1 used to derive the DXA profile in the DXA image data, the pixel position of the soft region of the DXA profile, and the pixel position of the bone region are predetermined according to, for example, the subject W and an imaging part.

In a case in which the derivation region R1 is not appropriately set in the derivation of the bone density, the accuracy of deriving the bone density is reduced. For example, in some cases, gas generated in the body of the subject W is included in the first radiographic image and the second radiographic image. In a case in which the derivation region R1 includes a region including the gas, it is difficult to distinguish the bone tissues from the soft tissues in the DXA image due to the influence of the gas. As a result, the accuracy of deriving bone density is reduced. In addition, for example, in a case in which the transverse process is present in the bone of the subject W and the derivation region R1 includes a region including the transverse process, the accuracy of deriving bone density is reduced by the influence of the transverse process.

For this reason, for example, the derivation region R1 is appropriately set so as not to include gas or the transverse process in order to increase the accuracy of deriving bone density.

Therefore, in the derivation of the bone density, the console 18 according to this embodiment has a function of reducing a burden on the user who performs a derivation operation of confirming the derivation region R1 and resetting the derivation region R1 on the basis of the confirmation result to assist the user.

Next, a process of reducing a burden on the user performing the bone density derivation operation in the console 18 will be described as the operation of the console 18 according to this embodiment.

Figure 8:
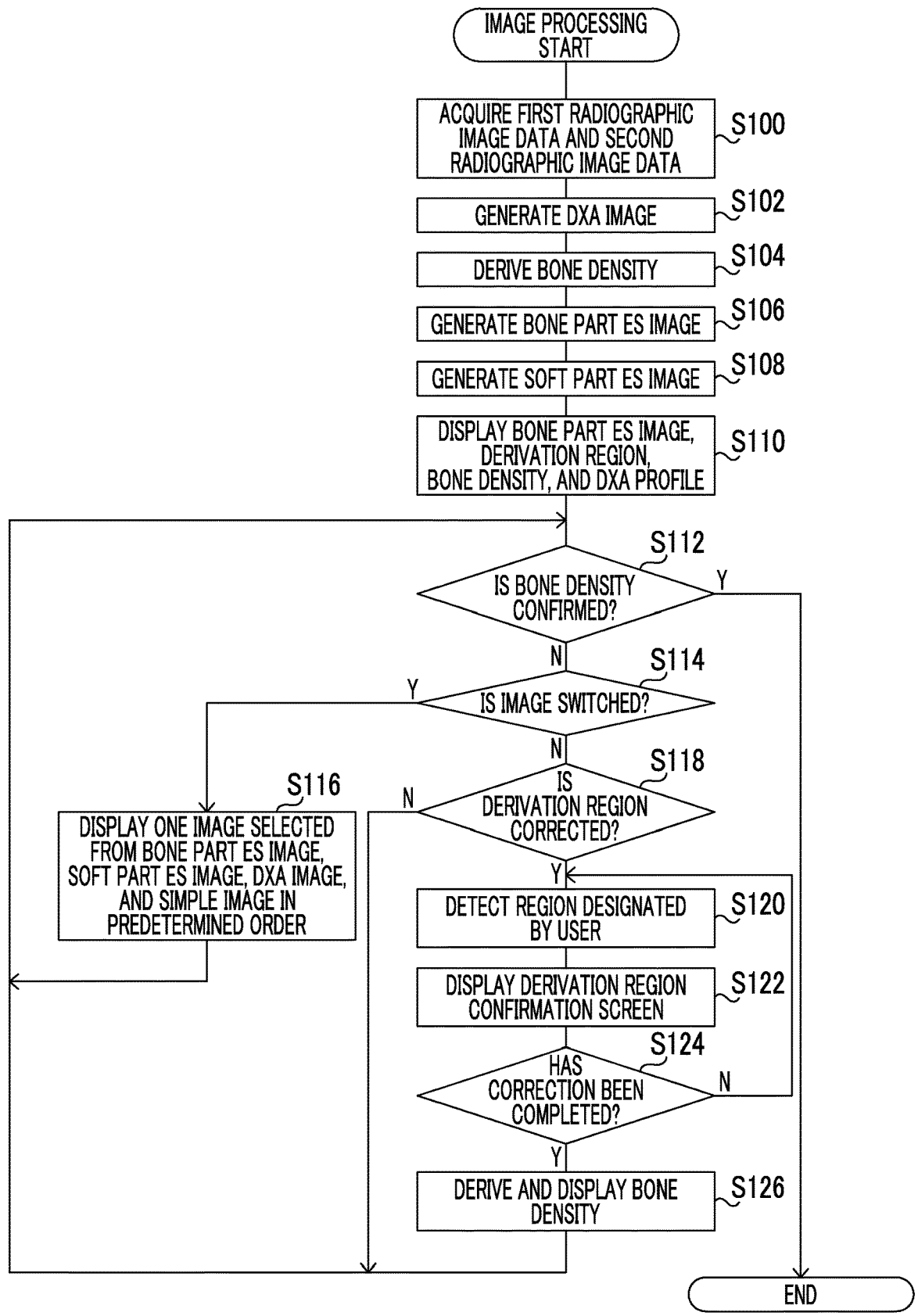
FIG. 8 is a flowchart illustrating an example of the flow of image processing performed by a control unit of a console according to the first embodiment.

FIG. 8 is a flowchart illustrating an example of the flow of image processing performed by the control unit 80 of the console 18 according to this embodiment. In a case in which the user inputs a command to derive bone density through the operation unit 94, the control unit 80 of the console 18 according to this embodiment executes an image processing program stored in the ROM 84 to perform the image processing illustrated in FIG. 8. In addition, in a case in which the CPU 82 of the control unit 80 according to this embodiment executes the image processing program, the control unit 80 according to this embodiment functions as an example of an acquisition unit, a derivation unit, a control unit, and a receiving unit according to the present disclosure.

In Step S100 of FIG. 8, the control unit 80 acquires first radiographic image data and second radiographic image data. The acquisition destination of the first radiographic image data and the second radiographic image data is not particularly limited. For example, in a case in which the first radiographic image data and the second radiographic image data received from the radiography apparatus 16 have been stored in the storage unit 88 in advance, the control unit 80 may acquire the first radiographic image data and the second radiographic image data from the storage unit 88. In addition, for example, the control unit 80 may directly acquire the first radiographic image data and the second radiographic image data from the radiography apparatus 16.

Then, in Step S102, as described above, the control unit 80 generates DXA image data (DXA image) using the first radiographic image data and the second radiographic image.

Then, in Step S104, as described above, the control unit 80 derives bone density using the DXA image data. In a case in which the control unit 80 derives bone density in Step S104, a method for extracting the derivation region R1 from the DXA image is not particularly limited. For example, in a case in which bone density is measured, an imaging part (bone) of the subject W is generally predetermined. Therefore, a predetermined region may be extracted on the basis of the position of the imaging part and may be set as the derivation region R1.

Then, in Step S106, the control unit 80 generates image data indicating a bone part energy subtraction image (hereinafter, referred to as an "ES image") in which the bone tissues have been highlighted. Hereinafter, the image data is referred to as "bone part ES image data". A method for generating the bone part ES image data is not particularly limited. For example, the control unit 80 may subtract image data obtained by multiplying the first radiographic image data by a predetermined coefficient for the bone part from image data obtained by multiplying the second radiographic image data by a predetermined coefficient for the bone part for each corresponding pixel to generate bone part ES image data indicating a bone part ES image in which the soft tissues have been removed and the bone tissues have been highlighted. As such, the bone part ES image according to this embodiment is a difference image between the first radiographic image and the second radiographic image in which the bone tissues have been highlighted and is an example of a bone part difference image according to the present disclosure.

Then, in Step S108, the control unit 80 generates image data (hereinafter, referred to as "soft part ES image data") indicating a soft part ES image in which the soft tissue is highlighted. A method for generating the soft part ES image data is not particularly limited. For example, the control unit 80 may subtract image data obtained by multiplying the first radiographic image data by a predetermined coefficient for the soft part from image data obtained by multiplying the second radiographic image data by a predetermined coefficient for the soft part for each corresponding pixel to generate soft part ES image data indicating a soft part ES image in which the bone tissues have been removed and the soft tissues have been highlighted. Here, the soft part ES image data can be generated by the same method as the bone part ES image data, using a predetermined coefficient for the soft part different from a predetermined coefficient for the bone part. As such, the soft part ES image according to this embodiment is a difference image between the first radiographic image and the second radiographic image in which the soft tissues have been highlighted and is an example of a soft part difference image according to the present disclosure.

Figure 9:
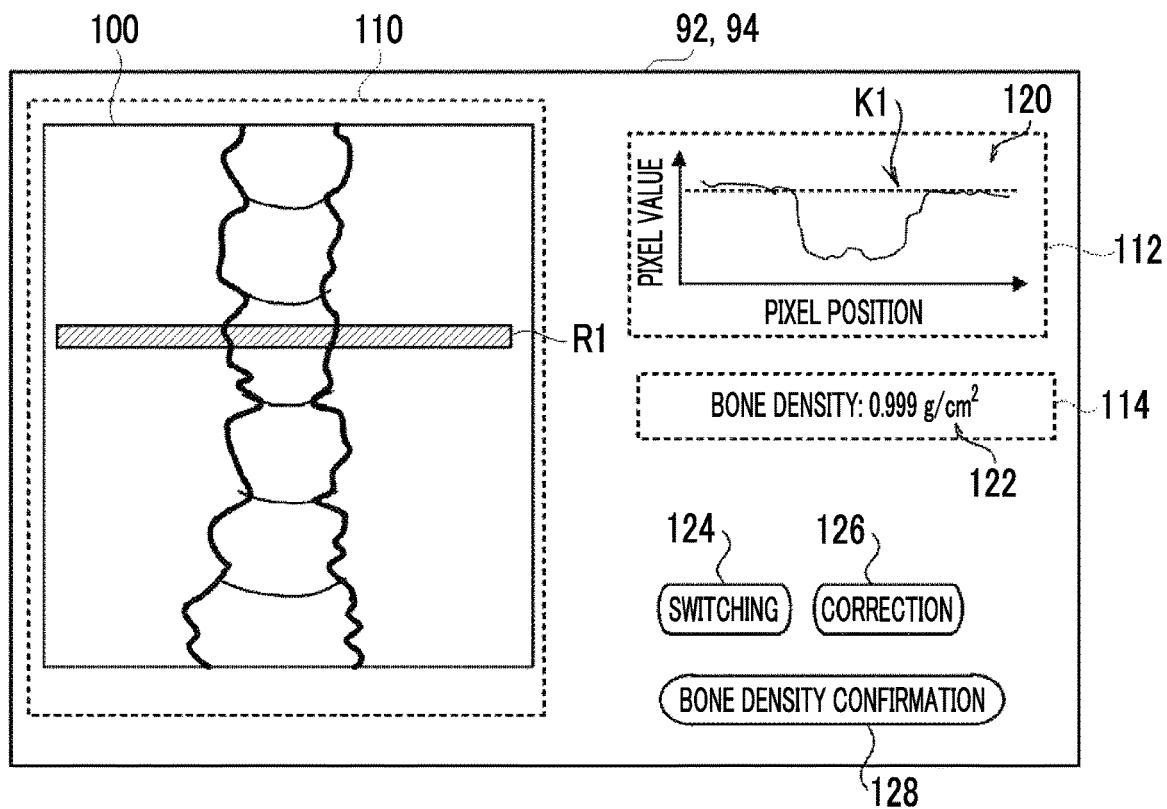
FIG. 9 is a diagram illustrating an example of a state in which a bone part ES image, a derivation region, bone density, and a DXA profile are displayed on a display unit.

Then, in Step S110, the control unit 80 displays the bone part ES image, the derivation region R1, the bone density, and the DXA profile on the display unit 92. FIG. 9 is a diagram illustrating an example of a state in which the bone part ES image, the derivation region R1, the bone density, and the DXA profile are displayed on the display unit 92.

FIG. 9 illustrates a state in which a bone part ES image 100 is displayed in an image display region 110 of the display unit 92. As illustrated in FIG. 9, an image indicating the derivation region R1 used to derive bone density in Step S104 is superimposed on the bone part ES image 100. In addition, FIG. 9 illustrates a state in which a DXA profile 120 used to derive bone density in Step S104 is displayed in a profile display region 112 and bone density information 122 indicating the bone density derived in Step S104 is displayed in a bone density display region 114.

In addition, as illustrated in FIG. 9, a switching button 124, a correction button 126, and a confirmation button 128 are displayed on the display unit 92. The switching button 124 is designated by the user through the operation unit 94 in a case in which the image displayed in the image display region 110 is switched. The correction button 126 is designated by the user through the operation unit 94 in a case in which the setting of the derivation region R1 is corrected (reset). The confirmation button 128 is designated by the user through the operation unit 94 in a case in which the derived bone density is confirmed as the bone density of the subject W.

Then, in Step S112, the control unit 80 determines whether the bone density has been confirmed. In this embodiment, in a case in which the confirmation button 128 is not designated by the user even after a predetermined period of time has elapsed since the process has proceeded to Step S112 and in a case in which the switching button 124 or the correction button 126 is designated by the user, the determination result in Step S112 is "No" and the process proceeds to Step S114. In Step S114, the control unit 80 determines whether to switch the image displayed in the image display region 110 to another image. In this embodiment, the determination result in Step S114 is "Yes" in a case in which the switching button 124 is designated by the user within a predetermined period of time after the process proceeds to Step S114 and the process proceeds to Step S116.

Figure 10:
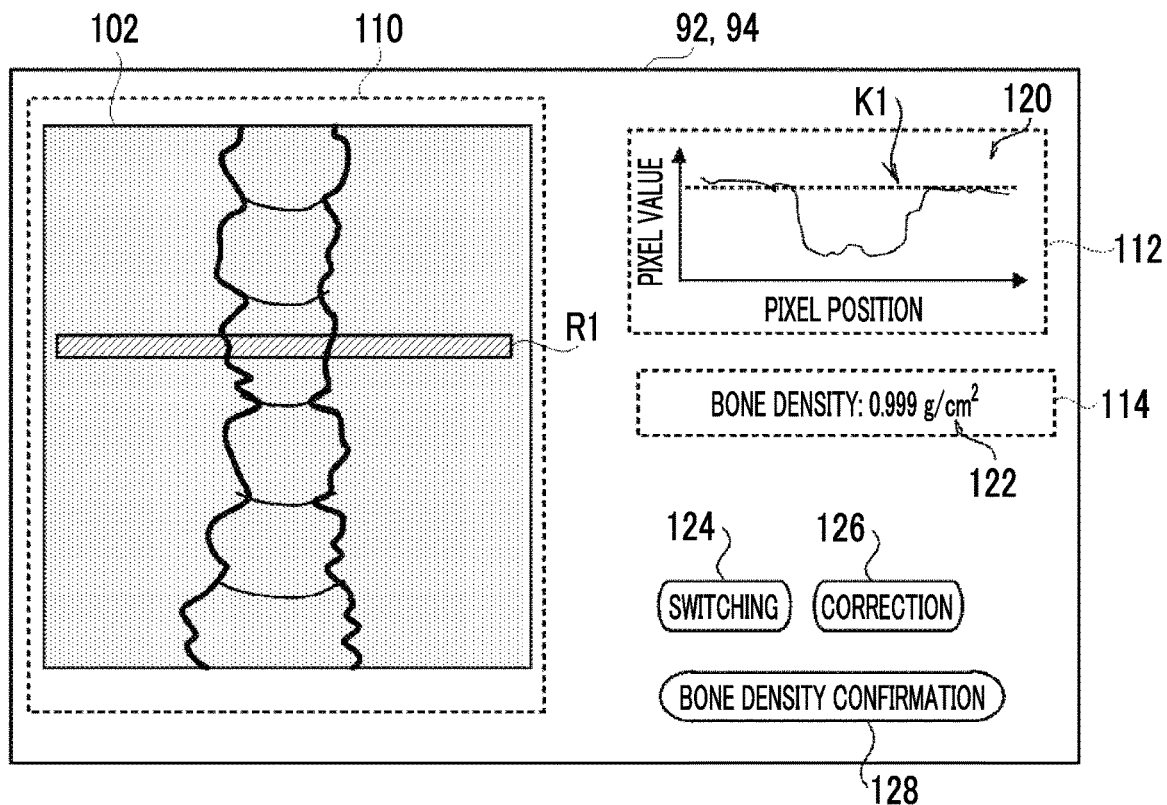
FIG. 10 is a diagram illustrating an example of a state in which an image displayed in an image display region is switched from the bone part ES image to a soft part ES image.

In Step S116, the control unit 80 performs a control process of displaying one image selected from the bone part ES image 100, a soft part ES image 102 (see FIG. 10, a DXA image 104 (see FIG. 13), and a simple image 106 (see FIG. 13) in a predetermined order in the image display region 110. In addition, the control unit 80 performs a control process of displaying the derivation region R1 so as to be superimposed on the switched image displayed in the image display region 110.

Figure 13:
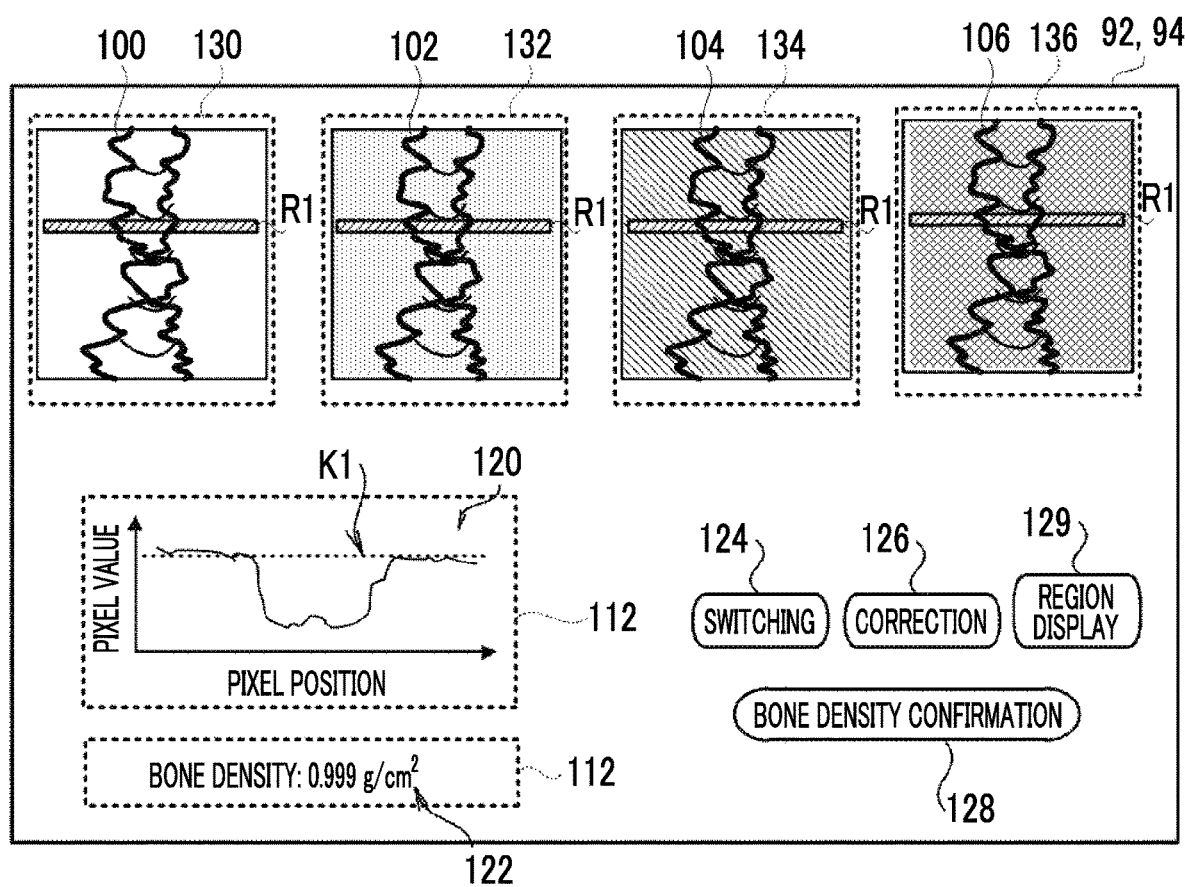
FIG. 13 is a diagram illustrating an example of a state in which a bone part ES image, a soft part ES image, a DXA image, a simple image, a derivation region, bone density, and a DXA profile are displayed on the display unit.

In this embodiment, for example, the predetermined order is the order of the bone part ES image 100, the soft part ES image 102, the DXA image 104 (see FIG. 13), and the simple image 106 (see FIG. 13). Specifically, for example, in a case in which the bone part ES image 100 is displayed in the image display region 110 as illustrated in FIG. 9, the control unit 80 switches the image displayed in the image display region 110 from the bone part ES image 100 to the soft part ES image 102. In a case in which the simple image 106 (see FIG. 13) which is the last in the predetermined order is displayed in the image display region 110, the control unit 80 switches the image displayed in the image display region 110 from the simple image 106 (see FIG. 13) to the bone part ES image 100. For example, FIG. 10 illustrates a state in which the image displayed in the image display region 110 has been switched from the bone part ES image 100 to the soft part ES image 102. In the example illustrated in FIG. 10, the image displayed in the image display region 110 is switched from the bone part ES image 100 to the soft part ES image 102. However, there is no change in display in the profile display region 112 and the bone density display region 114.

In this embodiment, the first radiographic image is displayed as the simple image on the display unit 92. However, the image displayed as the simple image is not limited to the first radiographic image and may be, for example, the second radiographic image. Alternatively, the first radiographic image and the second radiographic image may be displayed while being switched.

In a case in which the control unit 80 switches the image displayed in the image display region 110 in Step S116, the process returns to Step S112. As such, in this embodiment, whenever the switching button 124 is designated by the user, the control unit 80 switches the image displayed in the image display region 110 until the confirmation button 128 is designated by the user.

Since the bone tissues are highlighted in the bone part ES image, the bone part ES image makes it easy to understand the contour of the bone. Therefore, for example, it is easy to recognize whether the transverse process is present in the subject W. In a case in which the transverse process is present, it is easy to recognize the position of the transverse process. In addition, since the soft tissues are highlighted in the soft part ES image, the soft part ES image makes it easy to recognize the influence of the soft tissues. The soft part ES image makes it easy to recognize whether gas is generated in the subject W. In a case in which gas is generated, the soft part ES image makes it easy to recognize the position where gas is generated. Since the DXA image is actually used to derive bone density, it is easy to recognize the influence of the DXA image on the derivation of bone density. The simple image is used to diagnose, for example, the osteoporosis of the subject W and has a lower contrast as the bone part ES image, the soft part ES image, and the DXA image. However, in some cases, the simple image is easier to see than other images, depending on the content of diagnosis. The image used as the simple image is not particularly limited. One or both of the first radiographic image and the second radiographic image may be used as the simple image. That is, for example, the simple image may be predetermined for the user's desired purpose. For example, since the first radiographic image generated by the radiation detector (the first radiation detector 20A in this embodiment) close to the radiation source 14 is an image corresponding to low-energy radiation, the first radiographic image has a higher contrast than the second radiographic image. Therefore, the first radiographic image makes it easy to recognize, for example, the contour of the subject W. For this reason, it may be predetermined that the first radiographic image is used as the simple image. In addition, for example, the user may set the simple image, using the operation unit 94.

As described above, the control unit 80 according to this embodiment switches the image displayed in the image display region 110 and displays the image that is easily seen by the user in the image display region 110 in response to the user's designation.

On the other hand, in a case in which the switching button 124 is not designated by the user even after the predetermined period of time has elapsed since the process has proceeded to Step S114 or in a case in which the correction button 126 is designated by the user, the determination result in Step S114 is "No" and the control unit 80 proceeds to Step S118.

In Step S118, the control unit 80 determines whether the user has corrected the derivation region R1. As described above, in a case in which an appropriate region is not set as the derivation region R1, the accuracy of the derived bone density is reduced. Therefore, the console 18 according to this embodiment enables the user to correct (reset) the derivation region R1 to an appropriate region, considering the image displayed in the image display region 110. In a case in which the derivation region R1 is corrected (reset), the user designates the correction button 126 through the operation unit 94.

In this embodiment, in a case in which the correction button 126 is not designated by the user even after a predetermined period of time has elapsed since the process has proceeded to Step S118 and in a case in which the switching button 124 or the confirmation button 128 is designated by the user, the determination result in Step S118 is "No" and the process returns to Step S112. On the other hand, in a case in which the correction button 126 is designated, the determination result in Step S118 is "Yes" and the process proceeds to Step S120.

In Step S120, the control unit 80 detects a region that has been designated as the derivation region R1 by the user through the operation unit 94. How the user designates a region as the derivation region R1 and a method for detecting the region designated by the user are not particularly limited.

For example, in a case in which the display unit 92 and the operation unit 94 are integrated into a touch panel display, the user may trace the image displayed in the image display region 110 with a finger to designate a region as the derivation region R1. In this case, for example, the control unit 80 may detect the position of the image traced by the finger of the user and may detect an image (pixel) region in a predetermined range from the detected position as the derivation region R1.

Figure 11:
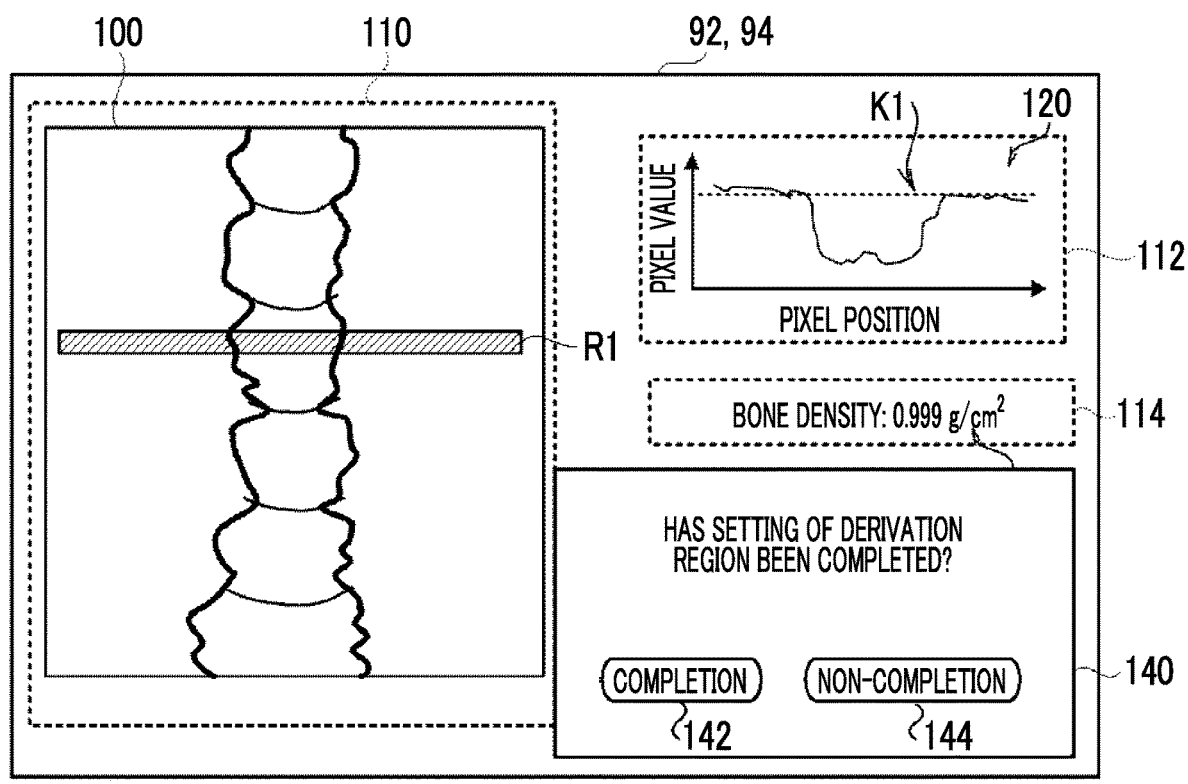
FIG. 11 is a diagram illustrating an example of a state in which a completion confirmation screen is displayed on the display unit in the state illustrated in FIG. 9.

Then, in Step S122, the control unit 80 displays a completion confirmation screen that enables the user to confirm whether the reset of the derivation region R1 has been completed on the display unit 92. For example, FIG. 11 illustrates a state in which the completion confirmation screen 140 is displayed on the display unit 92 in the state illustrated in FIG. 9. As illustrated in FIG. 11, a completion button 142 and a non-completion button 144 are displayed on the completion confirmation screen 140.

Then, in Step S124, the control unit 80 determines whether the correction (reset) of the derivation region R1 has been completed. In this embodiment, in a case in which the user designates the non-completion button 144 through the operation unit 94, the determination result in Step S124 is "No" and the process returns to Step S120. The reset of the derivation region R1 is repeated. On the other hand, in a case in which the user designates the completion button 142 through the operation unit 94, the determination result in Step S124 is "Yes" and the process proceeds to Step S126.

In Step S126, the control unit 80 derives bone density on the basis of the detected derivation region R1, that is, the derivation region R1 reset by the user, similarly to Step S104. In addition, the control unit 80 displays the derived bone density on the display unit 92. Specifically, the control unit 80 according to this embodiment displays information indicating the bone density displayed in the bone density display region 114 in information indicating the bone density derived in Step S126.

On the other hand, in a case in which the user designates the confirmation button 128 displayed on the display unit 92 in Step S112, the determination result in Step S112 is "Yes" and the control unit 80 ends the image processing.

At the end of the image processing, the control unit 80 may store at least one of the DXA image generated in Step S102, the bone part ES image generated in Step S106, or the soft part ES image generated in Step S108 in the storage unit 88 so as to be associated with the subject W. In addition, the derived (finally derived) bone density and information indicating the position of the derivation region R1 used to derive the bone density may be stored so as to be associated with each other.

In this embodiment, the aspect in which one image is displayed in the image display region 110 while being switched has been described. However, the number of images displayed in the image display region 110 is not limited to this embodiment. For example, a plurality of images of different types (for example, the bone part ES image 100 and the soft part ES image 102) may be displayed in the image display region 110 and each group of the plurality of images may be displayed in the image display region 110 while being switched.

In this embodiment, the image displayed in the image display region 110 is switched at the time designated by the user. However, the time when the image displayed in the image display region 110 is switched is not particularly limited. For example, whenever a predetermined period of time elapses, the control unit 80 may perform a control process of automatically switching the image displayed in the image display region 110 in the predetermined order. In addition, for example, buttons corresponding to the bone part ES image, the soft part ES image, the DXA image, and the simple image may be displayed on the display unit 92 and an image corresponding to the button selected by the user through the operation unit 94 may be displayed in the image display region 110 while being switched.

For example, the control unit 80 may perform a control process of detecting a region indicated by the user through the operation unit 94 in the image displayed in the image display region 110 of the display unit 92 and displaying any one of the simple image, the bone part ES image, the soft part ES image, and the DXA image predetermined according to the tissue corresponding to the detected region in the image display region 110. For example, in a case in which the user indicates a region corresponding to the bone tissues in the image displayed in the image display region 110, the possibility that the user will check the bone tissues is high. Therefore, the control unit 80 performs a control process of displaying the bone part ES image 100 in the image display region 110. In contrast, in a case in which the user indicates a region corresponding to the soft tissues in the image displayed in the image display region 110, the possibility that the user will check the soft tissues is high. Therefore, the control unit 80 performs a control process of displaying the soft part ES image 102 in the image display region 110. In addition, for example, on the contrary to the above, in a case in which the user indicates the region corresponding to the bone tissues in the image displayed in the image display region 110, the possibility that the user will check, for example, gas superimposed on the bone tissues in the image is high. Therefore, the control unit 80 performs a control process of displaying the soft part ES image 102 in the image display region 110. In contrast, in a case in which the user indicates the region corresponding to the soft tissues in the image displayed in the image display region 110, the possibility that the user will want to remove the bone tissues in order to designate the soft region is high. Therefore, the control unit 80 performs a control process of displaying the bone part ES image 100 in the image display region 110. Which of the above-mentioned aspects is used may be predetermined or the above-mentioned aspects may be switched in response to a command from the user. In these cases, the control unit 80 is an example of a detection unit according to the present disclosure.

As such, in this embodiment, the control unit 80 of the console 18 performs a control process that displays a plurality of images predetermined from the simple image which is at least one of the first radiographic image or the second radiographic image, the bone part ES image which is a difference image between the first radiographic image and the second radiographic image and in which the bone tissues have been highlighted, the soft part ES image which is a difference image between the first radiographic image and the second radiographic image and in which the soft tissues have been highlighted, and the DXA image on the display unit 92 while switching the images and a control process that displays the derivation result of the bone density and the derivation region R1 on the display unit 92.

As described above, the image (pixel value) of the soft region, such as the DXA image, is used to derive bone mineral content and bone density. Here, in a case in which the soft region is not an appropriate region, for example, in a case in which a factor has an adverse effect on the derivation result of bone density or bone mineral content is included in the image of the soft region, the accuracy of deriving bone density or bone mineral content is likely to be reduced. In this case, the user that derives bone density or bone mineral content manually sets a new derivation region R1 in, for example, the DXA image, the first radiographic image, and the second radiographic image. At that time, in some cases, it is difficult to see the images and to set the derivation region R1.

In contrast, the console 18 according to this embodiment displays the images without a factor having an effect on the derivation of bone density, such as the transverse process or gas generated in the body of the subject W, on the display unit 92 while switching the images such that the user easily sees the images. Therefore, it is possible to reduce a burden on the user performing the bone density derivation operation.

Second Embodiment

In the first embodiment, the aspect in which the control unit 80 of the console 18 displays the bone part ES image 100, the soft part ES image 102, the DXA image, and the simple image in the image display region 110 of the display unit 92 one by one while switching the images in this order has been described. In this embodiment, an aspect in which the bone part ES image 100, the soft part ES image 102, the DXA image, and the simple image are displayed side by side on the display unit 92 will be described.

Since the configuration of a radiography system 10 according to this embodiment is the same as that of the radiography system 10 (see FIGS. 1 to 4) according to the first embodiment, the description thereof will not be repeated. In this embodiment, since image processing performed by the control unit 80 of the console 18 is partially different from the image processing (see FIG. 8) according to the first embodiment, the image processing performed by the control unit 80 according to this embodiment will be described.

Figure 12:
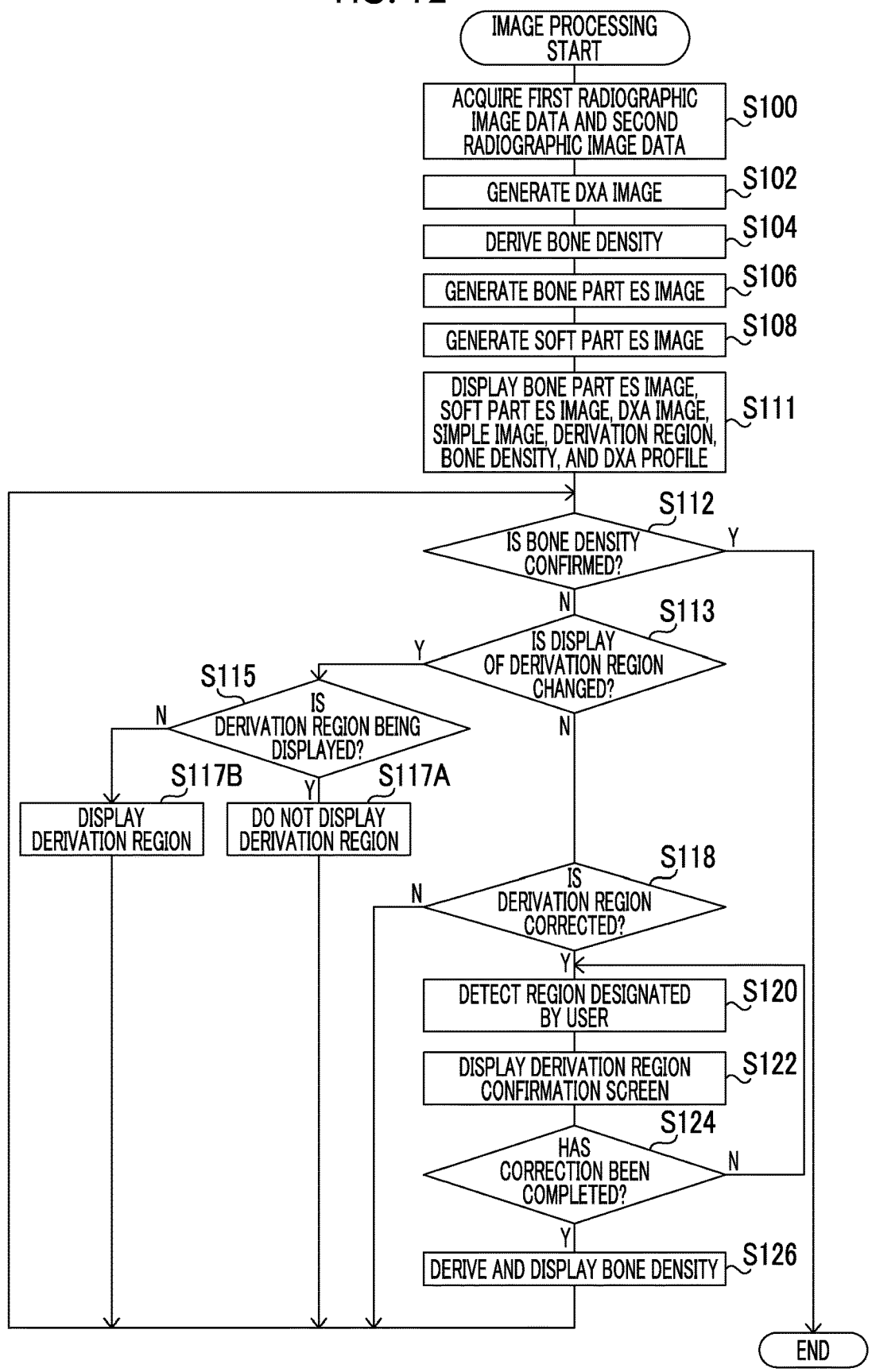
FIG. 12 is a flowchart illustrating an example of the flow of image processing performed by a control unit of a console according to a second embodiment.

FIG. 12 is a flowchart illustrating an example of the flow of the image processing performed by the control unit 80 according to this embodiment. As illustrated in FIG. 12, the image processing according to this embodiment is different from the image processing (see FIG. 8) according to the first embodiment in that Step S111 is performed instead of Step S110.

As illustrated in FIG. 12, in Step S111, the control unit 80 displays the bone part ES image 100, the soft part ES image 102, the DXA image, the simple image, the derivation region R1, the bone density, and the DXA profile on the display unit 92. FIG. 13 is a diagram illustrating an example of a state in which the bone part ES image 100, the soft part ES image 102, the DXA image 104, the simple image 106, the derivation region R1, the bone density, and the DXA profile are displayed on the display unit 92.

In the example illustrated in FIG. 13, the display unit 92 is provided with four image display regions (a first image display region 130, a second image display region 132, a third image display region 134, and a fourth image display region 136). FIG. 13 illustrates a state in which the bone part ES image 100 is displayed in the first image display region 130, the soft part ES image 102 is displayed in the second image display region 132, the DXA image 104 is displayed in the third image display region 134, and the simple image 106 is displayed in the fourth image display region 136. As illustrated in FIG. 13, an image indicating the derivation region R1 used to derive bone density in Step S104 is superimposed on each of the bone part ES image 100, the soft part ES image 102, the DXA image 104, and the simple image 106. In the example illustrated in FIG. 13, a region display button 129 is further displayed on the display unit 92.

In this embodiment, since four types of images, that is, the bone part ES image 100, the soft part ES image 102, the DXA image 104, and the simple image 106 are displayed as illustrated in FIG. 13, the user can compare the images at a time.

In addition, the image processing according to this embodiment is different from the image processing according to the first embodiment in that Steps S113, S115, S117A, and S117B are performed instead of Steps S114 and S116.

As illustrated in FIG. 12, in Step S113, the control unit 80 determines whether to change the display of an image indicating the derivation region R1. In this embodiment, in a case in which the user designates the region display button 129 displayed on the display unit 92 through the operation unit 94, the console 18 switches display between the display of the image indicating the derivation region R1 and the non-display of the image.

Figure 14:
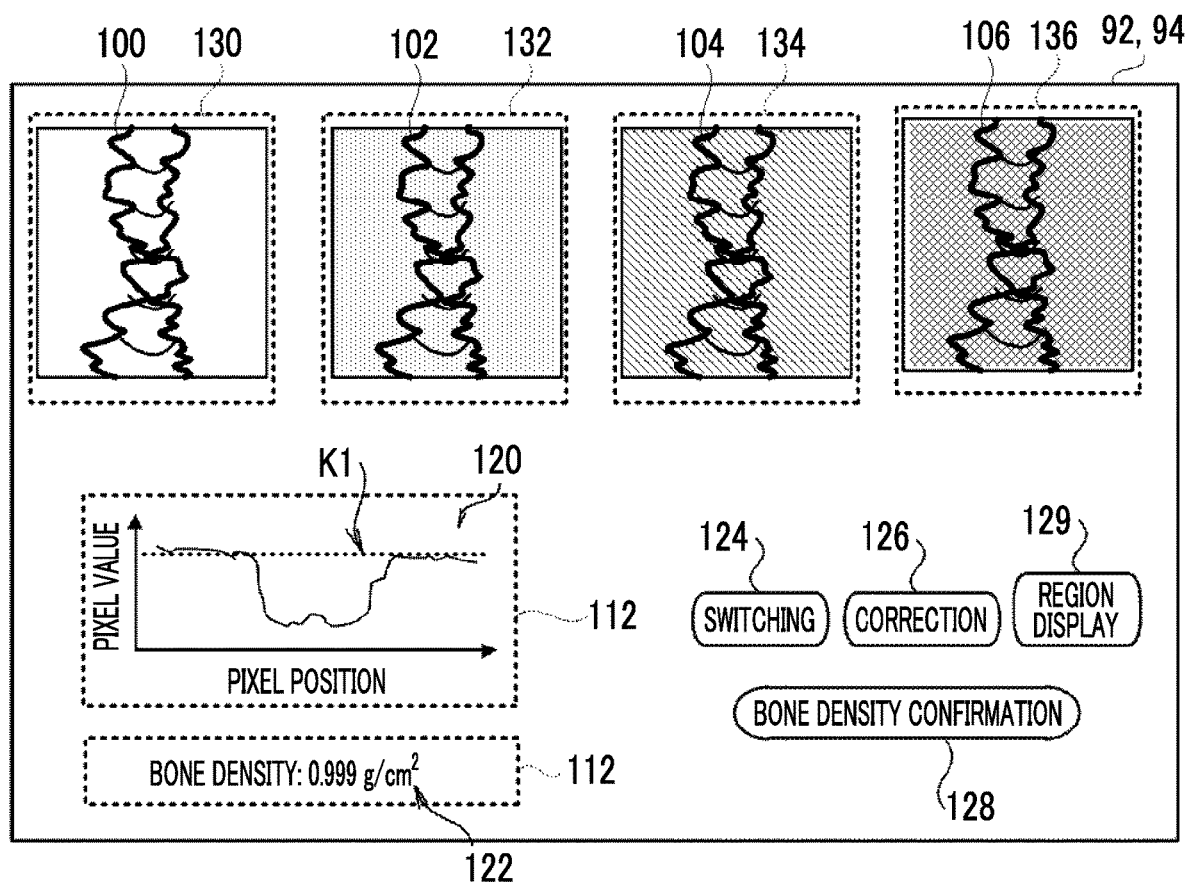
FIG. 14 is a diagram illustrating an example of a state in which the bone part ES image, the soft part ES image, the DXA image, the simple image, the bone density, and the DXA profile are displayed on the display unit.

In a case in which the user designates the region display button 129, the determination result in Step S113 is "Yes" and the process proceeds to Step S115. In Step S115, the control unit 80 determines whether the image indicating the derivation region R1 is currently being displayed on the display unit 92. In a case in which the image indicating the derivation region R1 is being displayed, the determination result in Step S115 is "Yes" and the process proceeds to Step S117A. In Step S117A, for example, as illustrated in FIG. 14, the control unit 80 does not display the image indicating the derivation region R1. In this embodiment, in this case, all of the images indicating the derivation region R1 superimposed on each of the bone part ES image 100, the soft part ES image 102, the DXA image 104, and the simple image 106 are not displayed.

In a case in which the image indicating the derivation region R1 is not displayed, that is, in the non-display state as illustrated in FIG. 14, the determination result in Step S115 is "No" and the process proceeds to Step S117B. In Step S117B, the control unit 80 displays the image indicating the derivation region R1. Then, the display of the image indicating the derivation region R1 on the display unit 92 returns to the state illustrated in FIG. 13.

On the other hand, in a case in which the determination result in Step S113 is "No", the process proceeds to Step S118.

As such, in this embodiment, the control unit 80 of the console 18 performs a control process that displays a plurality of images predetermined from the simple image which is at least one of the first radiographic image or the second radiographic image, the bone part ES image which is a difference image between the first radiographic image and the second radiographic image and in which the bone tissues have been highlighted, the soft part ES image which is a difference image between the first radiographic image and the second radiographic image and in which the soft tissues have been highlighted, and the DXA image side by side on the display unit 92 and a control process that displays the derivation result of the bone density and the derivation region R1 on the display unit 92.

As such, similarly to the control unit 18 according to the first embodiment, the console 18 according to this embodiment displays the images without a factor having an effect on the derivation of bone density, such as the transverse process or gas generated in the body of the subject W, side by side on the display unit 92 such that the user easily sees the images. Therefore, it is possible to reduce a burden on the user performing the bone density derivation operation.

For example, the configuration and operation of the radiography system 10, the radiography apparatus 16, and the console 18 described in each of the above-mentioned embodiments are illustrative and can be changed according to situations, without departing from the scope and spirit of the invention.

Figure 15:
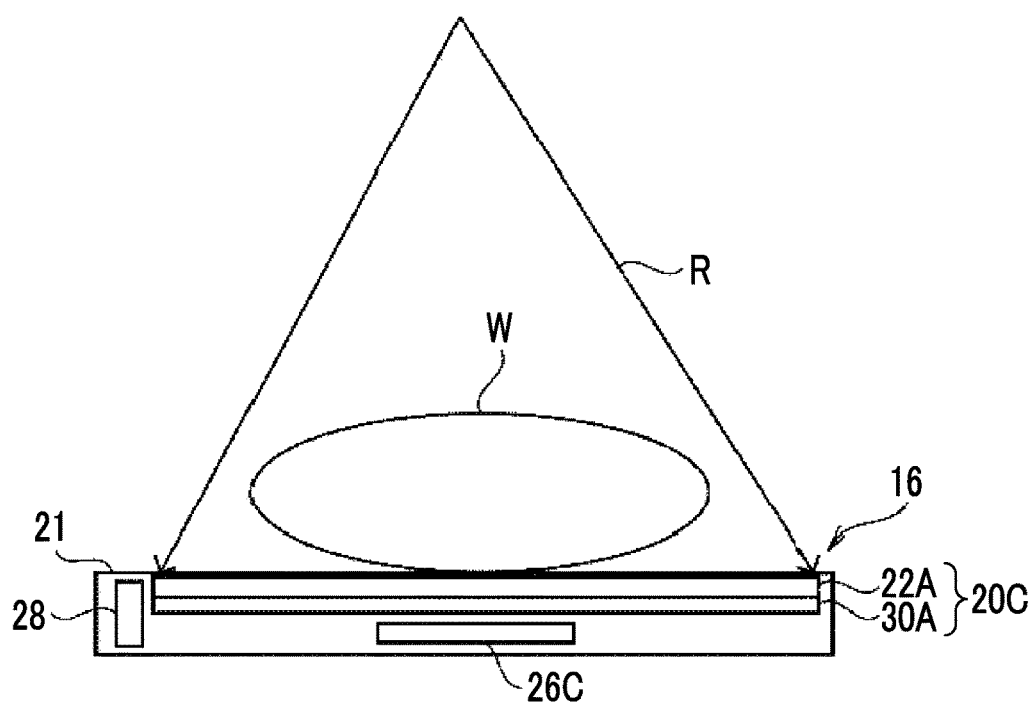
FIG. 15 is a side cross-sectional view illustrating another example of the configuration of the radiography apparatus.

For example, in the above-described embodiments, the radiography apparatus 16 includes two radiation detectors. However, for example, as illustrated in FIG. 15, the radiography apparatus 16 may include a single radiation detector. In the example illustrated in FIG. 15, a radiation detector 20C that detects the radiation R transmitted through the subject W and a control substrate 26C are provided in the housing 21 of the radiography apparatus 16. The configuration of the radiation detector 20C is the same as that of the first radiation detector 20A according to the first embodiment and the configuration of the control substrate 26C is the same as that of the control substrate 26A according to the first embodiment. Therefore, the description thereof will not be repeated here.

In the radiography apparatus 16 illustrated in FIG. 15, two radiography operations are performed at different tube voltages from the radiation emitting apparatus 12 and bone density is derived on the basis of radiographic image data captured by the radiation detector 20C in the two radiography operations. Since different tube voltages are used in the two radiography operations, the radiation detector 20C is irradiated with the radiations R having different energy levels.

Figure 16:
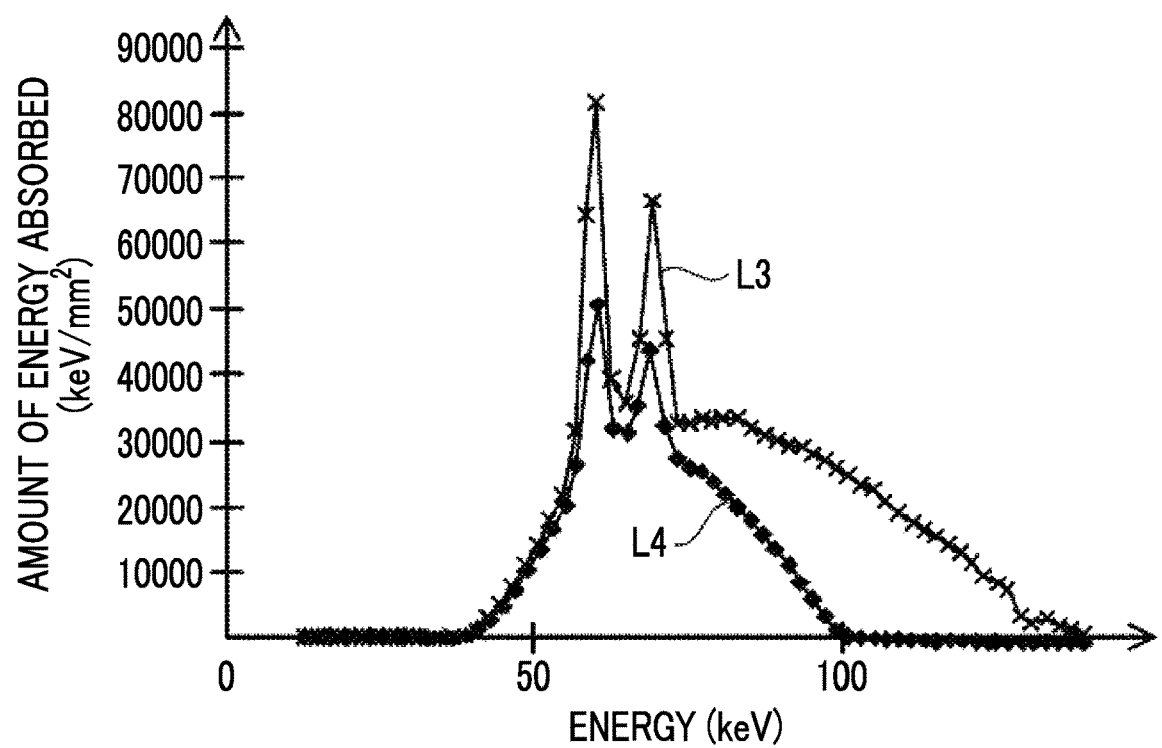
FIG. 16 is a graph illustrating the amount of radiation absorbed by a radiation detector in a case in which radiation is emitted at different tube voltages.

The radiation R absorbed by the radiation detector 20C will be described with reference to FIG. 16. In FIG. 16, the vertical axis indicates the amount of radiation R absorbed per unit area and the horizontal axis indicates the energy of the radiation R. In addition, in FIG. 16, a solid line L3 indicates the relationship between the energy of the radiation R absorbed by the radiation detector 20C and the amount of radiation R absorbed per unit area in a case in which the tube voltage of the radiation source 14 is 140 kV. In FIG. 16, a solid line L4 indicates the relationship between the energy of the radiation R absorbed by the radiation detector 20C and the amount of radiation R absorbed per unit area in a case in which the tube voltage of the radiation source 14 is 100 kV. As illustrated in FIG. 16, since the tube voltages of the radiation source 14 are different from each other, the radiation detector 20C is irradiated with the radiations R having different energy levels in first irradiation and second irradiation.

In each of the above-described embodiments, the bone part ES image, the soft part ES image, the DXA image, and the simple image are displayed on the display unit 92. However, the image displayed on the display unit 92 is not limited to these images. For example, the control unit 80 may display a plurality of images selected from the bone part ES image, the soft part ES image, the DXA image, and the simple image in the image display region 110 of the display unit 92 while switching the images. For example, in a case in which the bone density of the subject W has been derived in the past and some of the images used to derive the bone density remain, the control unit 80 may perform a control process of displaying the past images on the display unit 92.

In each of the above-described embodiments, the image indicating the derivation region R1 is displayed in the image display region 110 of the display unit 92 so as to be superimposed on the displayed image and information indicating bone density is displayed in the bone density display region 114. However, the invention is not limited thereto. For example, the control unit 80 may start image processing and may display the image indicating the derivation region R1 or the image indicating bone density on the display unit 92 first. For example, in a case in which the image indicating bone density is displayed first, the derivation region R1 is not displayed, and the user has some doubts about the bone density value and designates the image through the operation unit 94, the control unit 80 may display the derivation region R1.

In each of the above-described embodiments, the bone density derivation process or the image display process performed by the console 18 may be performed by the control unit 58A or the control unit 58B of the radiography apparatus 16. In addition, in a case in which the radiography apparatus 16 includes an overall control unit that controls the overall operation of the control unit 58A and the control unit 58B, the overall control unit may perform the bone density derivation process or the image display process. Furthermore, for example, an image processing apparatus that is connected to the console 18 through the network may perform the bone density derivation process or the image display process.

In the first embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (CdTe).

In the first embodiment, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In each of the above-described embodiments, the case in which bone density is derived using the first radiographic image data and the second radiographic image data has been described. However, the invention is not limited thereto. For example, bone mineral content or both bone density and bone mineral content may be derived using the first radiographic image data and the second radiographic image data. In a case in which bone mineral content is derived, the derivation region R1 is extracted from the DXA image similarly to the derivation of the bone density. Therefore, the same task as that in the case in which the bone density is derived occurs. As a result, for example, the same effect as that in each of the above-described embodiments is obtained in a case in which the bone mineral content is derived instead of the bone density in each of the above-described embodiments.

In each of the above-described embodiments, the image processing performed by the execution of software (program) by the CPU 82 of the control unit 80 may be performed by various processors other than the CPU 82. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the image processing may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which the image processing program is stored (installed) in the ROM 84 in advance has been described. However, the invention is not limited thereto. The image processing program may be recorded on a recording medium, such as a compact disk read only memory (CD-ROM), a digital versatile disk read only memory (DVD-ROM), or a universal serial bus (USB) memory, and then provided. In addition, the image processing program may be downloaded from an external apparatus through the network.

What is claimed is:

1. An image processing apparatus comprising:
   an acquisition unit that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;
   a derivation unit that derives at least one of bone mineral content or bone density from a derivation region of a difference image for derivation which is a difference image between the first radiographic image and the second radiographic image and is used to derive at least one of the bone density or the bone mineral content; and
   a control unit that performs a control process of displaying a plurality of images that correspond to a single subject and that are predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result of the derivation unit or the derivation region on the display unit,
   wherein the derivation unit is configured to derive the at least one of bone mineral content or bone density based on a difference image profile that indicates a relationship between a position of a pixel and a pixel value in the derivation region, by deriving an average value of pixel values in soft tissue regions on both sides of a bone tissue region, deriving an area of a bone region, dividing the area of the bone region by a number of pixels corresponding to a width of the bone region, and multiplying a difference between pixel values of the bone region and pixel values of the soft tissue region, per unit number of pixels, by a predetermined unit conversion coefficient.

2. An image processing apparatus comprising:
   an acquisition unit that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged;
   a derivation unit that derives at least one of bone mineral content or bone density from a derivation region of a difference image for derivation which is a difference image between the first radiographic image and the second radiographic image and is used to derive at least one of the bone density or the bone mineral content; and
   a control unit that performs a control process of displaying a plurality of images that correspond to a single subject and that are predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result of the derivation unit or the derivation region on the display unit,
   wherein the derivation unit is configured to derive the at least one of bone mineral content or bone density based on a difference image profile that indicates a relationship between a position of a pixel and a pixel value in the derivation region, by deriving an average value of pixel values in soft tissue regions on both sides of a bone tissue region, deriving an area of a bone region, dividing the area of the bone region by a number of pixels corresponding to a width of the bone region, and multiplying a difference between pixel values of the bone region and pixel values of the soft tissue region, per unit number of pixels, by a predetermined unit conversion coefficient.

3. An image processing apparatus comprising:
   an acquisition unit that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;

a derivation unit that derives at least one of bone mineral content or bone density from a derivation region of a difference image for derivation which is a difference image between the first radiographic image and the second radiographic image and is used to derive at least one of the bone density or the bone mineral content; and a control unit that performs a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side simultaneously on a single display unit and a control process of displaying at least one of a derivation result of the derivation unit or the derivation region on the display unit.

4. An image processing apparatus comprising:
an acquisition unit that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged;

a derivation unit that derives at least one of bone mineral content or bone density from a derivation region of a difference image for derivation which is a difference image between the first radiographic image and the second radiographic image and is used to derive at least one of the bone density or the bone mineral content; and a control unit that performs a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side simultaneously on a single display unit and a control process of displaying at least one of a derivation result of the derivation unit or the derivation region on the display unit.

5. The image processing apparatus according to claim 1, further comprising:
a detection unit that detects a region indicated by a user in the image displayed on the display unit, wherein the control unit performs a control process of displaying any one of the at least one of the first radiographic image or the second radiographic image, the bone part difference image in which the bone tissue is highlighted, the soft part difference image, and the difference image for derivation which has been predetermined according to a tissue corresponding to the region detected by the detection unit on the display unit.

6. The image processing apparatus according to claim 5, wherein the control unit performs a control process of displaying the bone part difference image on the display unit in a case in which the region detected by the detection unit corresponds to the bone tissue and displaying the soft part difference image on the display unit in a case in which the region detected by the detection unit corresponds to the soft tissue.

7. The image processing apparatus according to claim 5, wherein the control unit performs a control process of displaying the soft part difference image on the display unit in a case in which the region detected by the detection unit corresponds to the bone tissue and displaying the bone part difference image on the display unit in a case in which the region detected by the detection unit corresponds to the soft tissue.

8. The image processing apparatus according to claim 1, wherein the control unit performs a control process of further displaying a profile indicating a relationship between a pixel position and a pixel value in the derivation region on the display unit.

9. The image processing apparatus according to claim 1, wherein the control unit performs a control process of displaying at least the derivation region so as to be superimposed on the image displayed on the display unit.

10. The image processing apparatus according to claim 1, further comprising:
a receiving unit that receives a change in the derivation region,
wherein, in a case in which the receiving unit receives the change, the derivation unit derives at least one of the bone mineral content or the bone density from the changed derivation region.

11. The image processing apparatus according to claim 1, wherein each of the first and second radiation detectors comprises a light emitting layer that is irradiated with the radiation and emits light,
the plurality of pixels of each of the first and second radiation detectors receive the light, generate the charge, and accumulate the charge, and
the light emitting layer of one of the first and second radiation detectors which is provided on an incident side of the radiation includes CsI and the light emitting layer of the other radiation detector includes GOS.

12. A radiography system comprising:
the image processing apparatus according to claim 1; and
a radiography apparatus that outputs a first radiographic image and a second radiographic image to the image processing apparatus.

13. An image processing method comprising:
acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;

deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images that correspond to a single subject and that are predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result or the derivation region on the display unit, wherein deriving the at least one of bone mineral content or bone density is based on a difference image profile that indicates a relationship between a position of a pixel and a pixel value in the derivation region, and includes deriving an average value of pixel values in soft tissue regions on both sides of a bone tissue region, deriving an area of a bone region, dividing the area of the bone region by a number of pixels corresponding to a width of the bone region, and multiplying a difference between pixel values of the bone region and pixel values of the soft tissue region, per unit number of pixels, by a predetermined unit conversion coefficient.

14. An image processing method comprising:

acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged;

deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images that correspond to a single subject and that are predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation on a display unit while switching the images and a control process of displaying at least one of a derivation result or the derivation region on the display unit, wherein deriving the at least one of bone mineral content or bone density is based on a difference image profile that indicates a relationship between a position of a pixel and a pixel value in the derivation region, and includes deriving an average value of pixel values in soft tissue regions on both sides of a bone tissue region, deriving an area of a bone region, dividing the area of the bone region by a number of pixels corresponding to a width of the bone region, and multiplying a difference between pixel values of the bone region and pixel values of the soft tissue region, per unit number of pixels, by a predetermined unit conversion coefficient.

15. An image processing method comprising:

acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;

deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side simultaneously on a single display unit and a control process of displaying at least one of a derivation result or the derivation region on the display unit.

16. An image processing method comprising:

acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged;

deriving at least one of bone mineral content or bone density from a derivation region of a difference image for derivation which is a difference image between the first radiographic image and the second radiographic image and is used to derive at least one of the bone density or the bone mineral content; and performing a control process of displaying a plurality of images predetermined from at least one of the first radiographic image or the second radiographic image, a bone part difference image which is a difference image between the first radiographic image and the second radiographic image and in which a bone tissue is highlighted, a soft part difference image which is a difference image between the first radiographic image and the second radiographic image and in which a soft tissue is highlighted, and the difference image for derivation side by side simultaneously on a single display unit and a control process of displaying at least one of a derivation result or the derivation region on the display unit.

\* \* \* \* \*